(12) United States Patent
Fergason et al.

(10) Patent No.: US 7,553,021 B2
(45) Date of Patent: Jun. 30, 2009

(54) OPTICAL SYSTEM FOR MONITORING EYE MOVEMENT

(75) Inventors: James L. Fergason, Menlo Park, CA (US); John D. Fergason, Cupertino, CA (US)

(73) Assignee: Fergason Patent Properties, LLC, Menlo Park, CA (US)

( * ) Notice: Subject to any disclaimer, the term of this patent is extended or adjusted under 35 U.S.C. 154(b) by 0 days.

(21) Appl. No.: 11/906,672

(22) Filed: Oct. 2, 2007

(65) Prior Publication Data

US 2008/0030685 A1 Feb. 7, 2008

Related U.S. Application Data

(63) Continuation-in-part of application No. 10/753,085, filed on Jan. 7, 2004, now Pat. No. 7,347,551.

(60) Provisional application No. 60/447,395, filed on Feb. 13, 2003.

(51) Int. Cl.
*A61B 3/14* (2006.01)
*A61B 3/10* (2006.01)

(52) U.S. Cl. .................. 351/210; 351/209; 351/205

(58) Field of Classification Search ......... 351/205–246; 340/575, 576; 341/20, 21
See application file for complete search history.

(56) References Cited

U.S. PATENT DOCUMENTS

| 4,145,122 A | 3/1979 | Rinard et al. |
| 4,702,575 A | 10/1987 | Breglia et al. |
| 5,155,516 A | 10/1992 | Shindo |
| 5,182,443 A | 1/1993 | Suda et al. |
| 5,748,113 A | 5/1998 | Torch |
| RE36,237 E * | 6/1999 | Shindo ........................ 362/315 |
| 6,163,281 A * | 12/2000 | Torch ........................... 341/21 |
| 6,246,344 B1 | 6/2001 | Torch |
| 6,542,081 B2 | 4/2003 | Torch |
| 2001/0028309 A1 | 10/2001 | Torch |

FOREIGN PATENT DOCUMENTS

| DE | 29504973 U | 8/1996 |
| GB | 2385451 A | 8/2003 |
| JP | 11206713 A | 8/1999 |

* cited by examiner

*Primary Examiner*—Mohammed Hasan
(74) *Attorney, Agent, or Firm*—Cindy Kaplan (57) ABSTRACT

In one embodiment, a system for monitoring eye movement through optical observation of the eye includes an optical device configured for mounting on a frame for positioning the optical device on a user. The optical device includes a light source configured for emitting light along a first path and a sensor positioned in the optical device to receive light from a second path substantially parallel to the first path. A reflector is located within a lens connected to the frame and configured when positioned on the user to reflect light emitted by the light source onto the eye and reflect light reflected by the eye back to the sensor. The reflector covers only a portion of the lens.

20 Claims, 7 Drawing Sheets

ROTATE PARABOLA ABOUT FOCUS
R< = -27 DEGREES

OPTICAL SYSTEM FOR MONITORING EYE MOVEMENT

RELATED APPLICATIONS

The present application is a continuation-in-part of U.S. patent application Ser. No. 10/753,085, filed Jan. 7, 2004, which claims priority of U.S. Provisional Patent Application No. 60/447,395, filed Feb. 13, 2003, which are both incorporated herein by reference in their entirety.

BACKGROUND OF THE INVENTION

The present disclosure relates generally to monitoring movement of a human eye.

Drowsiness and fatigue while driving is a serious problem that leads to thousands of automobile crashes each year. Critical aspects of driving impairment associated with sleepiness include reaction time, attention, and information processing. Sleep related crashes are most common in young people, shift workers whose sleep is disrupted by working at night or working long or irregular hours, and people with untreated sleep apnea syndrome and narcolepsy.

There are some in-vehicle systems that are intended to measure sleepiness or some behavior associated with sleepiness in commercial and noncommercial driving. Examples include brain wave monitors, eye-closure monitors, devices that detect steering variance, and tracking devices that detect lane drift. For example, infrared cameras or other devices have been used to monitor a driver's awareness. These devices are typically mounted on the dashboard or roof of the driver's vehicle. Such devices, however, require that the driver maintain constant eye contact with the camera. In addition, they do not monitor eyelid movement if the user looks sideways or turns around. These cameras may also have difficulty seeing through eyeglasses or sunglasses and may not operate effectively in sunlight.

In addition to monitoring drowsiness of drivers, such systems are also needed for monitoring pilots or other individuals. One system that is independent from the vehicle is an eye movement monitoring system which is contained within a frame worn on a user's head. An example of this type of system is disclosed in U.S. Patent Application Publication No. US2001/0028309 A1, by William C. Torch. The system includes an array of emitters for directing light towards a person's eye and an array of sensors for detecting light from the array of emitters. The sensors detect light that is reflected off of the eye or eyelid, thus producing output signals indicating when the eye is covered by the eyelid. The emitters project a reference frame towards the eye, and a camera on the frame monitors movement of the eye relative to the reference frame. Such systems, however, are typically large, complex, and costly to manufacture. Furthermore, these systems may obstruct at least a portion of the user's view.

Eye monitoring systems are also used to track a user's eye to control electrical devices such as a computer input device (e.g., pointer or mouse) and for assistive technology for disability products. There are many different techniques which can be used for eye tracking. One conventional system is a remote mounted tracking device. A major drawback to this type of system is that it is not very effective when the user is actively moving their head or body independent of gazing at a point. Conventional head mounted eye tracking devices often require complex optics and processing equipment and are typically expensive to manufacture, heavy, making them difficult to wear for extended periods of time, and often obstruct at least a portion of a user's view.

SUMMARY OF THE INVENTION

In one embodiment, a system for monitoring eye movement through optical observation of the eye includes an optical device configured for mounting on a frame for positioning the optical device on a user. The optical device includes a light source configured for emitting light along a first path and a sensor positioned to receive light from a second path substantially parallel to the first path. A reflector is located within a lens connected to the frame and configured when positioned on the user to reflect light emitted by the light source onto the eye and reflect light reflected by the eye back to the sensor. The reflector covers only a portion of the lens.

Further understanding of the nature and advantages of the inventions herein may be realized by reference to the remaining portions of the specification and the attached drawings.

BRIEF DESCRIPTION OF THE DRAWINGS

Corresponding reference characters indicate corresponding parts throughout the several views of the drawings.

DESCRIPTION OF EXAMPLE EMBODIMENTS

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

The present disclosure is directed to a system for monitoring eye movement, and more specifically, the opening and closing of the eye or tracking of the eye to determine the direction of a user's gaze. Monitoring of the opening and closing of the eye may be used to detect drowsiness or sleepiness based on, for example, the number of blinks, time between blinks, or duration of eyelid closure. As described below, the system uses light to measure the frequency and speed of a human eye blink. Humans typically blink about 5-30 times per minute, with each blink lasting about 200-300 milliseconds. As a person gets tired or sleepy, eye blinks get longer and slower until the eyes begin to close for short periods. The system disclosed herein may be used, for example, by drivers, pilots, operators of heavy machinery, or other individuals to warn them when they are getting tired. The system may also be used in a laboratory environment to study individuals with sleep disorders or for medical research. Monitoring of the eye opening and closing may also be used to control electronic equipment, as described below. Tracking the gaze of the user's eye may be used alone or in combination with the monitoring of eyelid position to provide additional control of computers or other electronically controlled equipment.

The system is relatively small and lightweight as compared to conventional eye movement detection systems. Since the system is preferably contained within the frame, the data obtained from the optical device is not dependent upon movement of the user or the direction the user is looking.

Figure 1:
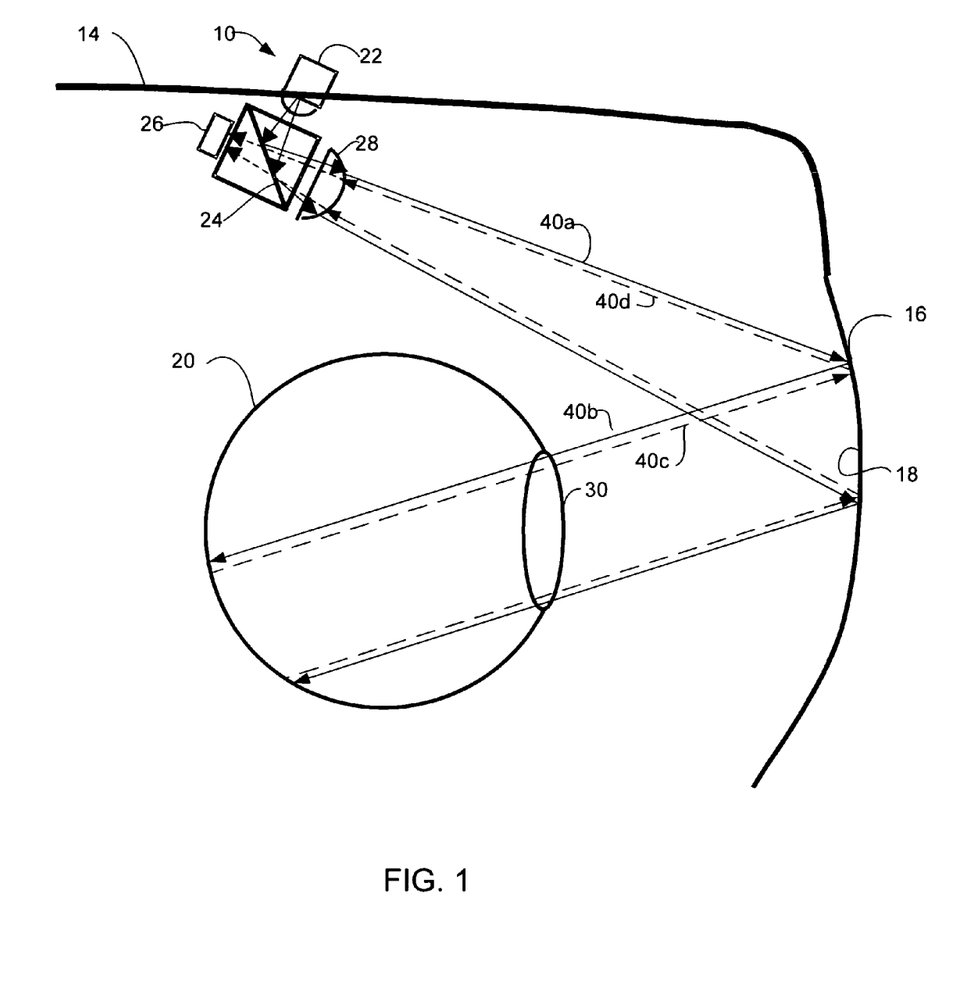
FIG. 1 is a schematic illustrating one embodiment of an optical system shown mounted relative to a user's eye.
Figure 4:
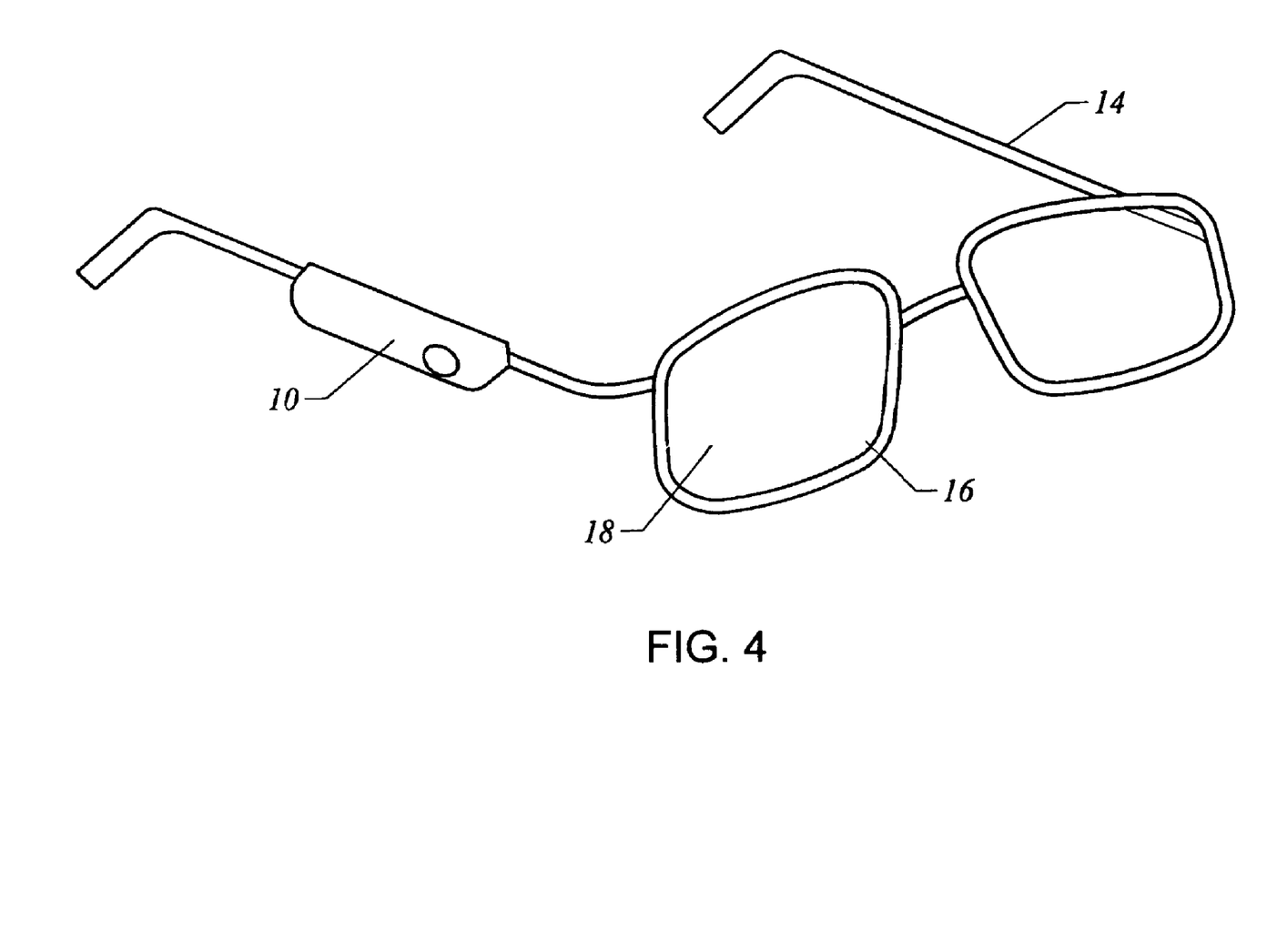
FIG. 4 is a perspective of an optical device mounted on an eyeglass frame.
Figure 5:
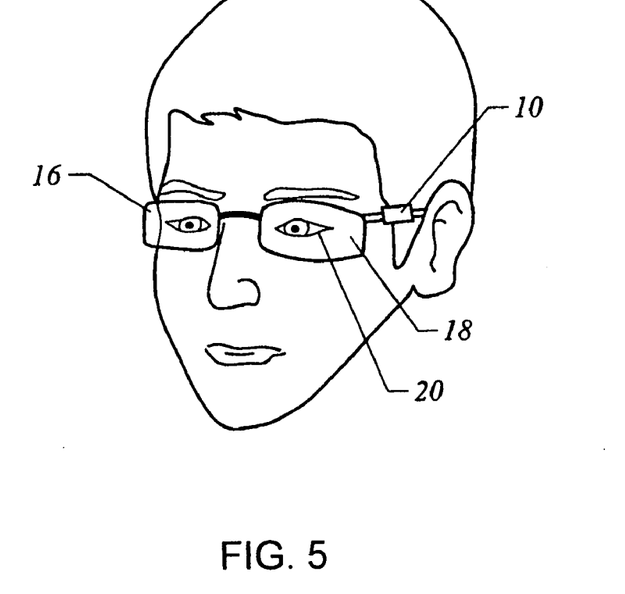
FIG. 5 is a perspective of the optical device and eyeglass frame of FIG. 3 mounted on a user's head.

Referring now to the drawings, and first to FIG. 1, one embodiment is schematically shown with an exemplary eye 20 (including retina, sclera, iris, lens, and cornea) of a user positioned relative to the system. The system includes an optical device 10 which is attached (either removably or fixedly) to a frame (e.g., eyeglasses) configured to be worn on a user (FIGS. 4 and 5). The frame may include a side member 14 and a pair of eyepieces (lenses) 16, at least one of which forms part of an optical path, as described below. The optical device 10 is preferably attached to the frame such that it is substantially unobtrusive to the user's view.

The system includes optical device 10 and a reflector (e.g., reflective member (surface)) 18, which is formed by a surface of the eyepiece 16 positioned opposite the eye 20 (FIG. 1). In one embodiment, the optical device 10 includes a light source 22, beamsplitter 24, sensor 26, and focusing optics (lens) 28. The light source 22 may comprise a Light Emitting Diode (LED) which emits an infrared beam. The emitted light is preferably within the infrared range (or near infrared range) to minimize interference with the user's vision since the infrared light is not visible to the user. The beamsplitter 24 is positioned to transmit at least some of the incident light emitted from the light source 22 to the reflective surface 18. One or more lenses 28 may be positioned to direct light received from the beamsplitter 24 onto reflective surface 18, as indicated by light ray 40a.

The sensor and light source are preferably integrally mounted in the optical device so that they are positioned generally at the same location on the frame. It is to be understood that the integrally mounted light source and sensor may be mounted in different locations within or on the optical device. The sensor is positioned to receive light from a path substantially parallel to the path that the light emitted from the light source travels.

The reflective member 18 of the eyepiece 16 receives light emitted from the light source 22 and reflects the light towards the eye 20 as light ray 40b. The reflective surface 18 may be formed by a dielectric or other type of coating. In one embodiment, the reflective surface 18 is a hot mirror. The hot mirror selectively separates infrared light from visible light. The infrared light is reflected by the hot mirror and light in the visible spectrum is transmitted through the surface 18. The reflective surface 18 may be configured to reflect light over a select range of wavelength (e.g., infrared or other suitable wavelengths). The reflector 18 is preferably both reflective and refractive.

The eyepiece 16 may have various curvatures and is shaped to provide optimum performance based on the approximate distance between the eyepiece and the eye 20 and optical device 10, as is well known by those skilled in the art.

In the embodiment shown in FIG. 1, the light rays travel after reflection by the eye in a direction that is generally parallel to that of the source of incident light. The light thus travels the same or substantially the same path, but in the opposite direction to respective incident light rays impinging on the eye.

Light exits the eye 20 (ray 40c) and is reflected by surface 18 back towards the optical device 10 (ray 40d). Sensor 26 is provided to detect light reflected from the eye 20. The light is reflected from the eyepiece 16 back to sensor 26, which is mounted on the frame. Due to differences in the reflective characteristics of the surface of the eye and the eyelid, the intensity of the light reflected off of the eye depends on whether the eye is open or closed. Light intensity signals corresponding to eyelid movement received from the sensor 26 are sent to a processor, which converts the received data into a suitable signal. The light intensity signals may be compared with a predetermined light intensity level to determine whether the eyelid is in an open or closed position. The sensor 26 may be, for example, a photodiode, photocell, photodetector, camera (described below), or other suitable device. One or a plurality of sensors 26 may be used. The sensor preferably includes a stop at the focal point of the parabola. The imaging device provides information as to where the pupil is positioned.

It is to be understood that the system shown in FIG. 1 is only one example and that other optical components, such as lenses, filters, reflectors, wave plates, apertures, stops, etc., may be used or the arrangement of components may be changed, without departing from the scope of the invention.

Figure 2A:
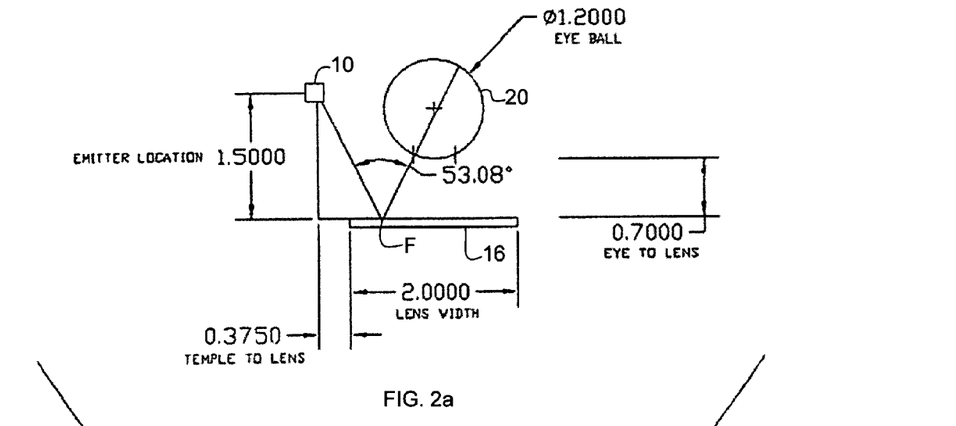
FIGS. 2a-2d illustrate one example of optical system geometry.
Figure 2B:
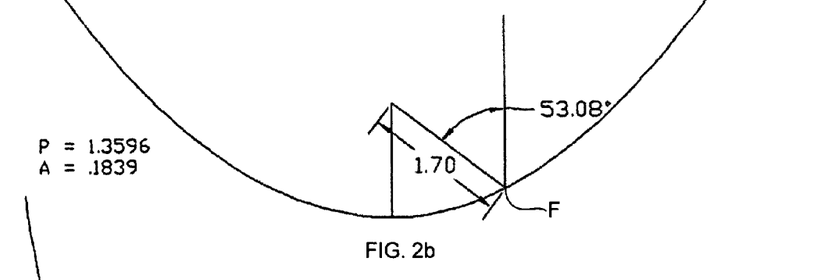
Figure 2C:
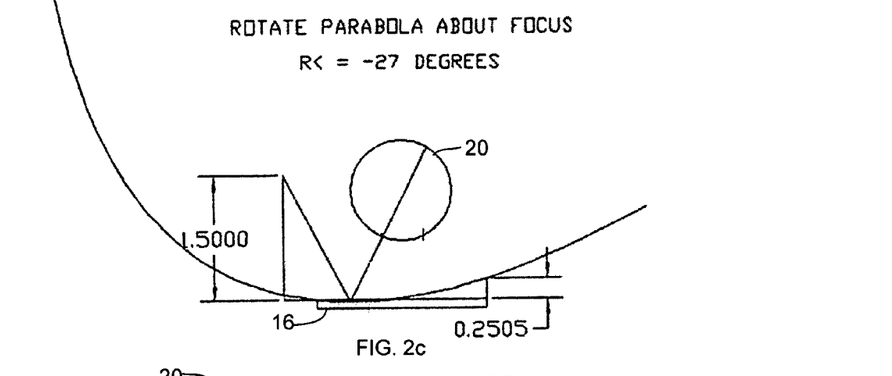
Figure 2D:
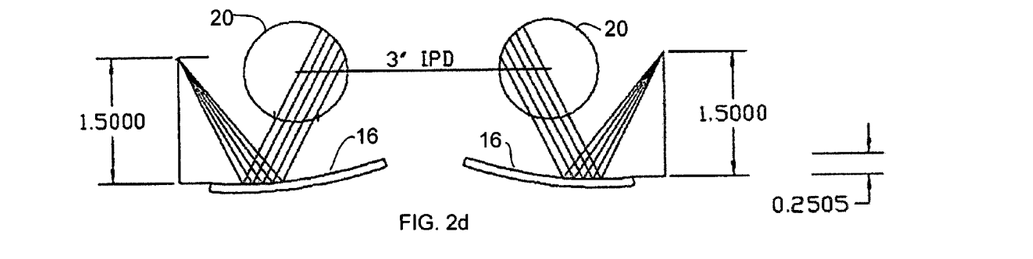

FIGS. 2a-2d illustrate an example of optical system geometry in accordance with one embodiment. In this embodiment, the starting assumptions are that the light emitter is positioned in the optical device 10 at a distance of approximately 1.5 inches from the lens 16, the width of the lens is approximately 2 inches, the distance between the temple and lens is approximately 0.375 inches, and the distance between the eye and lens is approximately 0.7 inches. The eyeball is assumed to have a diameter of approximately 1.2 inches. The light is reflected from the lens at focal point F at an angle of approximately 53.08 degrees. FIG. 2b illustrates a parabola defined by the geometry shown in FIG. 2a. The light is emitted over a distance of approximately 1.7 inches from the emitter to the lens. In FIG. 2c, the parabola is rotated about focal point F. A distance between one end of the lens and a parabola defining the focal point at the lens is approximately 0.25 inches. The lens may be shaped in accordance with this (or other suitable) geometry or a localized reflector, described below, may provide the desired characteristics.

Figure 3:
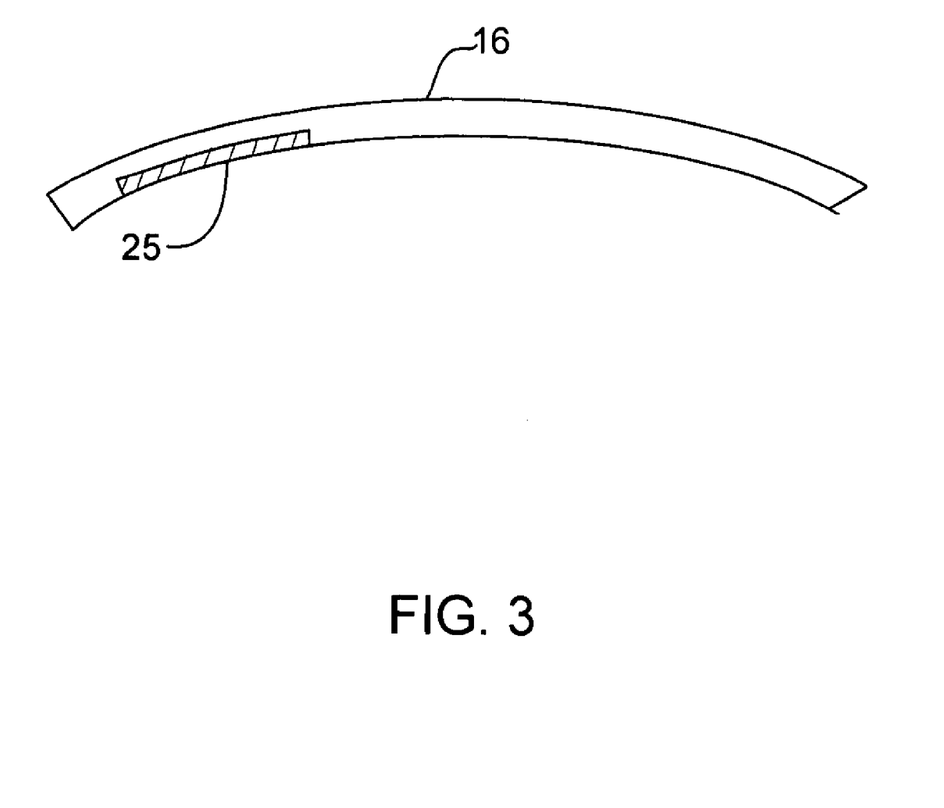
FIG. 3 illustrates an example of a lens comprising a reflector.

As described above, the reflector 18 is located within the lens 16. This includes a reflective member embedded in the lens 16, as shown in FIG. 3 and described below, or a reflective member mounted on the surface of the lens 16. The reflector 18 preferably covers only a portion of the lens 16 so that the geometry (e.g., radius of curvature, focal point) of the reflector may be different than the geometry of the lens 16. By localizing the reflector to only the area upon which light is reflected, the system can be adapted for use in various eye glass configurations and lens contours.

FIG. 3 illustrates one embodiment of a reflector 25 positioned at the reflection area of the lens 16. The reflector 25 is transparent to normal vision. The reflector 25 may be, for example, a parabolic reflector embedded within the lens by molding or other manufacturing techniques. In one embodiment, the lens is formed with a recess for receiving an insert.

The reflector 18 may also be removably attached to the lens. For example, the reflector 18 may be a sticker on the lens surface that provides an infrared reflector. In another embodiment, the reflector 18 is imprinted onto the lens surface. The reflector 18 may also be a holographic reflector.

Figure 6:
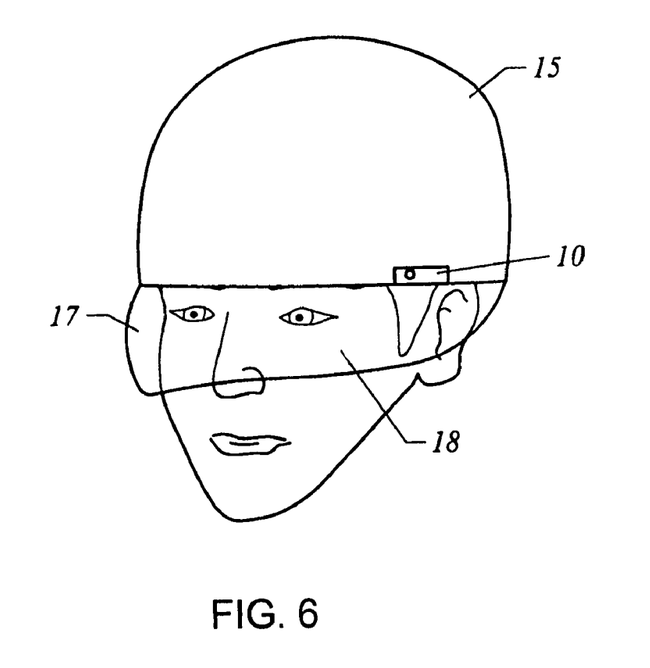
FIG. 6 is a perspective of the optical device mounted on a helmet worn on a user.

As shown in FIG. 6, the frame may comprise other user mounted equipment, such as a helmet 15. The helmet 15 includes a visor 17 which forms the eyepiece having the reflective surface 18 formed thereon. Only a portion of the visor 17 may be formed with a reflective surface, as required to reflect light transmitted from a light source onto the eye 20 and transmit light reflected from the eye to a sensor (described below). The remaining portion of the visor 17 may be transparent or tinted to reduce light intensity.

The systems shown in FIGS. 4, 5, and 6 include an optical device 10 positioned to monitor only one of the user's eyes 20. It is to be understood, however, that the system may also be configured with two optical devices 10, one for each eye 20. Also, it should be noted that the reflector 18 may be positioned anywhere within the lens 16 to provide the proper optical geometry corresponding to the position of the optical sensor.

Figure 7:
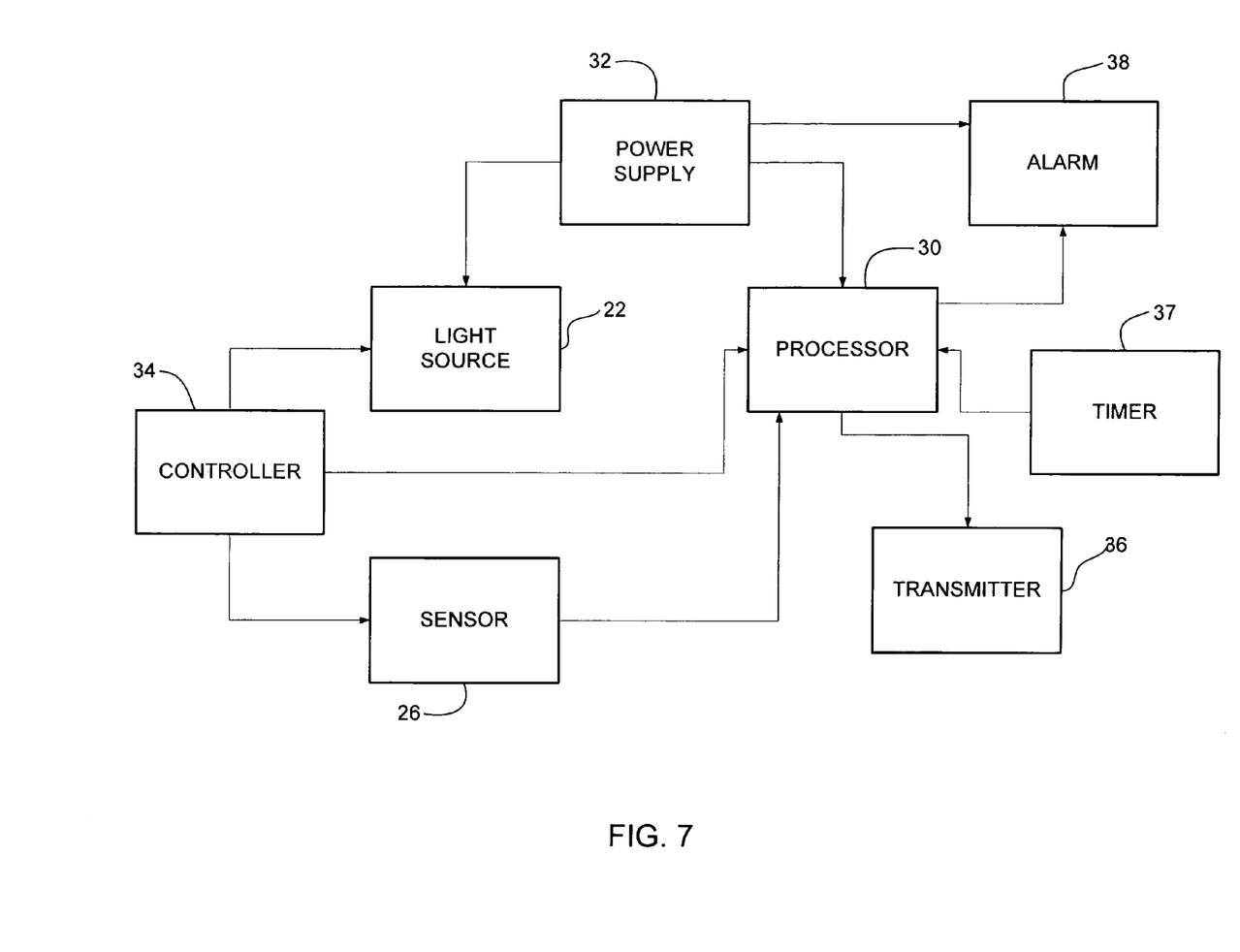
FIG. 7 is a block diagram illustrating electronic components of the optical system according to one embodiment.

Electronic circuitry and components of the system include a processor 30, power supply 32, controller 34, transmitter 36, timer 37, alarm 38, and other appropriate electronics required to transmit a signal detected based on eyelid position and provide proper operation of the optical system (FIG. 7). The controller 34 may be configured to control the intensity of light emitted by the light source 22, adjust the threshold sensitivity of the sensor 26, turn the light source on and off, or control the alarm 38. The controller 34 preferably controls the light source 22 to produce a signal pulsed at a predetermined frequency (e.g., 4-20 pulses per second). The sensor 26 may be synchronized to detect light pulses only at the predetermined frequency. The timer 37 provides a reference time for comparing the length of time between eyelid movements to a predetermined threshold. The timer function may also be provided by a clock of the processor 30. The power supply 32 provides power to the light source 22, sensor 26, processor 30, alarm 38, transmitter 36, and other components requiring a power source. The power supply 32 may be a conventional battery or any other suitable power source. Memory (not shown) may also be provided to store the data or signals for further analysis. The system may also include one or more digital filters as required to reduce noise.

The processor 30 is coupled to the sensor 26 for converting light intensity signals (e.g., binary code) corresponding to eyelid movement received from the sensor into data that can be processed and sent to the alarm 38. The processor 30 is configured to receive and process an output signal, such as a light intensity signal, from the sensor 26. The processor 30 may also include circuitry for the transmission of data and conversion of the data into various formats. Data may be sent from the transmitter 36 via a wire attached to the device and leading from the frame to a remote device (e.g., unit worn by user or unit mounted adjacent to or remote from the user) or wireless transmission may be used to send signals generated by the sensor 26 or processor 30 to a remote device using suitable frequencies. The transmitter 36 may be coupled to an amplifier if needed to send the signal to a remote device. The transmitter 36 may not be required if the alarm 38 is contained within the optical device 10 and coupled to the processor 30 or sensor 26, and if there is no need to send the data to a remote device for monitoring or analysis.

The alarm 38 may be activated when the sensor 26 detects eyelid closure for a minimum specified duration, when the frequency of eye blinks increases above a specified threshold, or the time between blinks reaches a predetermined limit. The alarm 38 may be initiated, for example, when a user begins blinking slower than normal for a specified period of time. The alarm 38 may provide an audible alarm, visual warning light, vibrating device, or any other suitable device which stimulates one or more senses of the user. The alarm 38 may be mounted directly on the optical device or frame to eliminate the need for remote transmission of data or signals, as previously discussed.

It is to be understood that the block diagram of the circuitry described above and shown in FIG. 7 is only one example and that different components and arrangement of components may be used, as is well known by those skilled in the art. Also, many of the functions shown independently in FIG. 7 may be grouped together as one or more components.

Figure 8:
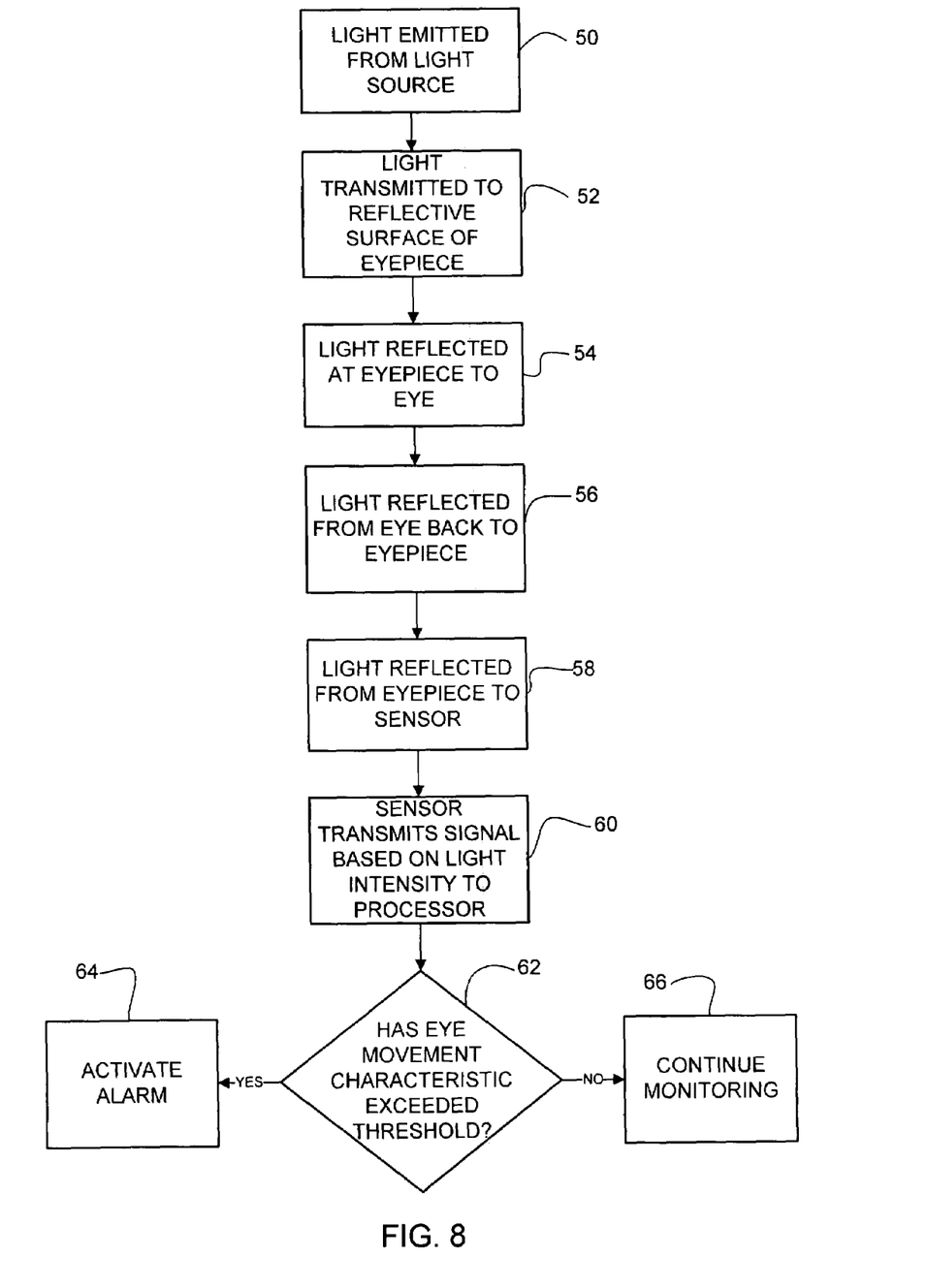
FIG. 8 is a flowchart illustrating operation of the optical system.

FIG. 8 is a flowchart illustrating an example of operation of the optical system described above. The light is first emitted from the light source 22 at step 50. The light is transmitted from the light source to the reflective surface 18 of the eyepiece 16 (step 52) and reflected from the eyepiece 16 to the eye 20 (step 54). The light is then reflected by the eye (step 56). The reflective surface 18 reflects the light towards the sensor 26 at step 58. The sensor 26 transmits a signal based on light intensity to the processor 30 (step 60). If the eye movement detected by the sensor 26 results in a selected characteristic (e.g., number of blinks, time between blinks, duration of eyelid closure) exceeding a predetermined threshold, the alarm 38 is activated (steps 62 and 64). The monitoring may then continue after the alarm is activated. If the eye movement does not result in an alarm condition, monitoring is continued (steps 62 and 66).

The system may also be configured to track eye movement to determine the direction of gaze of the user, in addition to or in place of tracking the opening and closing of the eyelid. The direction of gaze of the user's eye 20 or position of the eyelid may be used to provide input to a computer (e.g., mouse, pointer, scroll), control on/off functions for various electronic devices, or for assistive technology for disability products (e.g., wheelchair). For example, a pointer may be placed at a specific location on a computer screen by looking at a desired location. A click of a mouse may be provided with an eye blink or by staring (dwell) or instructions may be provided by monitoring the number of blinks. The system may also be used as a communication device. For example, data from the system may be sent to a device which converts the data into an audio output. The system may be configured to track the gaze of one or both eyes 20 or may track eyelid movement of one eye and the gaze of one eye, or any combination thereof.

In order to track the gaze of the user's eye 20, a camera is provided as the sensor 26. The camera is positioned as required to discern an image indicating the position of the eye. Additional optical components may be included. For example, a stop may be used to position the image properly. The camera may be a charge-coupled device (CCD) that provides an output image of the eye 20, which is processed by an image processor to determine the user's direction of gaze. The camera is electrically coupled to a computer for digitization and processing of the digitized image data. The position of the reflected image of the light source 22 is monitored relative to the center of the user's eye, as is well known by those skilled in the art. The image processing is used to interpret the position of the eyeball as observed by the camera. The position of the eyeball is identified by tracking the position of the pupil. One of the eye's visible features may also be used, such as the boundary between the sclera and iris or the outline of the pupil against the iris.

Although the present invention has been described in accordance with the embodiments shown, one of ordinary skill in the art will readily recognize that there could be variations made to the embodiments without departing from the scope of the present invention. Accordingly, it is intended that all matter contained in the above description and shown in the accompanying drawings shall be interpreted as illustrative and not in a limiting sense.

What is claimed is:

1. A system for monitoring eye movement through optical observation of the eye, the system comprising:
   an optical device configured for mounting on a frame for positioning the optical device on a user, the optical device comprising a light source configured for emitting light along a first path and a sensor positioned to receive light from a second path substantially parallel to said first path; and
   a reflector located within a lens connected to the frame and configured when positioned on the user to reflect light emitted by the light source onto the eye and reflect light reflected by the eye back to the sensor, wherein the reflector covers only a portion of the lens.

2. The system of claim 1 wherein the reflector is configured to reflect a limited range of wavelengths.

3. The system of claim 2 wherein the reflector is configured to reflect only infrared light.

4. The system of claim 1 wherein the reflector has a radius of curvature different than a radius of curvature of the lens.

5. The system of claim 1 wherein the lens comprises a recess for receiving the reflector.

6. The system of claim 5 wherein the reflector is a molded insert.

7. The system of claim 1 wherein the reflector is removably applied to a surface of the lens.

8. The system of claim 1 wherein the reflector is imprinted on a surface of the lens.

9. The system of claim 1 wherein the reflector is configured to detect light reflected by the eye in a direction that is substantially parallel to the light incident on the eye.

10. The system of claim 1 wherein the optical device is positioned on the frame such that it is a distance of 1.5 inches from the lens.

11. The system of 1 wherein the optical device is positioned on the frame and the reflector is configured such that light is reflected from the reflector at an angle of greater than 50 degrees relative to the light emitted from the optical device.

12. The system of claim 1 wherein a distance between one end of the lens and a parabola defining the focal point at the reflector is 0.25 inches.

13. The system of claim 1 further comprising a processor operable to convert an output signal from the sensor into a signal identifying a position of the eye.

14. A system for monitoring eye movement through optical observation of the eye, the system comprising:
   a frame configured to be worn on a user;
   an optical device connected to the frame and comprising a light source configured to emit light along a first path and a sensor positioned to receive light from a second path substantially parallel to said first path; and
   a lens connected to the frame and comprising a reflector configured when positioned on the user to reflect light emitted by the light source onto the eye and reflect light reflected by the eye back to the sensor, wherein the reflector covers only a portion of the lens.

15. The system of claim 14 wherein the optical device is positioned to monitor movement of one eye and further comprising:
   a second optical device positioned to monitor movement of the other eye; and
   a second lens comprising a second reflector.

16. The system of claim 14 wherein the reflector has a radius of curvature different than a radius of curvature of the lens.

17. The system of claim 14 wherein the reflector is configured to detect light reflected by the eye in a direction that is substantially parallel to the light incident on the eye.

18. The system of claim 14 further comprising a processor operable to convert an output signal from the sensor into a signal identifying a position of the eye.

19. The system of claim 14 wherein the reflector is configured to reflect a limited range of wavelengths.

20. The system of claim 19 wherein the reflector is configured to reflect only infrared light.

* * * * *